(12) United States Patent
Urbanski et al.

(10) Patent No.: US 10,456,234 B2
(45) Date of Patent: Oct. 29, 2019

(54) CONICAL VENA CAVA FILTER WITH JUGULAR OR FEMORAL RETRIEVAL

(71) Applicant: Cook Medical Technologies LLC, Bloomington, IN (US)

(72) Inventors: Jason C. Urbanski, Bloomington, IN (US); Lindsay Koren, Bloomington, IN (US); Sean Howard, Littleton, CO (US); Susan Kaiser, Neubiberg (DE); Thomas W. Jensen, Ballerup (DK)

(73) Assignee: COOK MEDICAL TECHNOLOGIES, INC., Bloomington, IN (US)

( * ) Notice: Subject to any disclaimer, the term of this patent is extended or adjusted under 35 U.S.C. 154(b) by 202 days.

(21) Appl. No.: 15/479,374

(22) Filed: Apr. 5, 2017

(65) Prior Publication Data

US 2017/0202656 A1    Jul. 20, 2017

Related U.S. Application Data

(62) Division of application No. 13/542,902, filed on Jul. 6, 2012, now Pat. No. 9,668,850.

(51) Int. Cl.
*A61F 2/01* (2006.01)

(52) U.S. Cl.
CPC .......... *A61F 2/01* (2013.01); *A61F 2002/016* (2013.01); *A61F 2220/0016* (2013.01); *A61F 2230/0067* (2013.01); *A61F 2230/0093* (2013.01)

(58) Field of Classification Search
CPC ...... A61F 2/01; A61F 2/013; A61F 2002/011; A61F 2002/016; A61F 2230/005; A61F 2220/0083
See application file for complete search history.

(56) References Cited

U.S. PATENT DOCUMENTS

| | | |
|---|---|---|
| 5,601,595 A | 2/1997 | Smith |
| 5,733,294 A | 3/1998 | Forber et al. |
| 6,506,205 B2 | 1/2003 | Goldberg et al. |
| 6,635,070 B2 | 10/2003 | Leeflang et al. |
| 6,656,202 B2 | 12/2003 | Papp et al. |
| 6,890,340 B2 | 5/2005 | Duane |
| 7,083,633 B2 | 8/2006 | Morrill et al. |
| 7,179,275 B2 | 2/2007 | McGuckin, Jr. et al. |
| 2002/0193827 A1 | 12/2002 | McGuckin, Jr. et al. |
| 2003/0163158 A1 | 8/2003 | White |
| 2004/0093012 A1 | 5/2004 | Cully et al. |
| 2005/0004596 A1 | 1/2005 | McGuckin, Jr. et al. |
| 2005/0015111 A1 | 1/2005 | McGuckin |
| 2006/0224180 A1 | 10/2006 | Anderson et al. |
| 2007/0032816 A1 | 2/2007 | O'Connell et al. |
| 2008/0188886 A1 | 8/2008 | Kusleika et al. |
| 2010/0023048 A1 | 1/2010 | Mach |
| 2010/0030254 A1 | 2/2010 | Chanduszko et al. |

*Primary Examiner* — Anh T Dang
(74) *Attorney, Agent, or Firm* — Brinks Gilson & Lione

(57) ABSTRACT

A removable intravascular filter having a filtering configuration for capturing thrombi in a blood vessel and a retrieval configuration for removal from the blood vessel. The filter may be implanted in a patient's vena cava and may be removed from the vena cava through the patient's jugular or femoral vein. A method of removing an intravascular filter from a patient's vena cava through the patient's femoral vein is also provided.

5 Claims, 8 Drawing Sheets

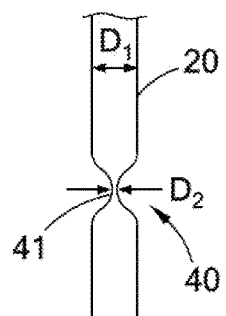
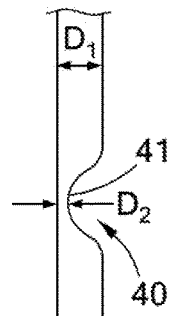
Fig. 2a    Fig. 2b
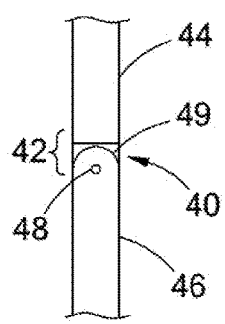
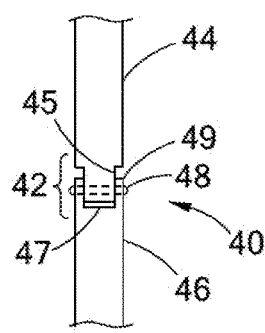
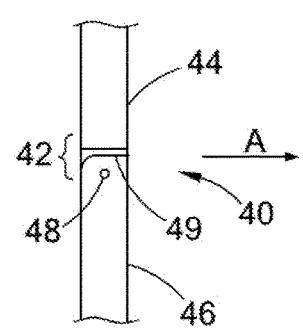
Fig. 3a    Fig. 3b    Fig. 3c

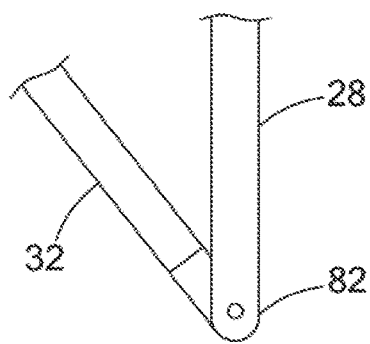
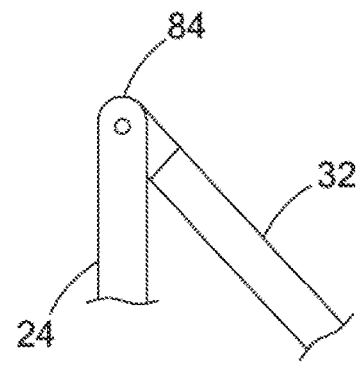
Fig. 4a    Fig. 4b
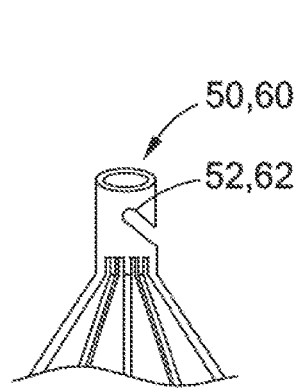
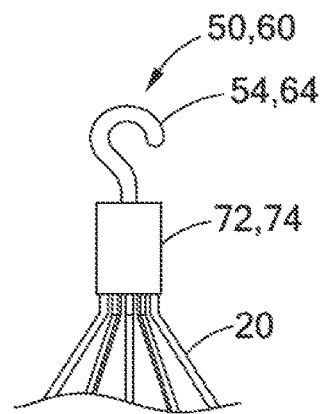
Fig. 5a    Fig. 5b

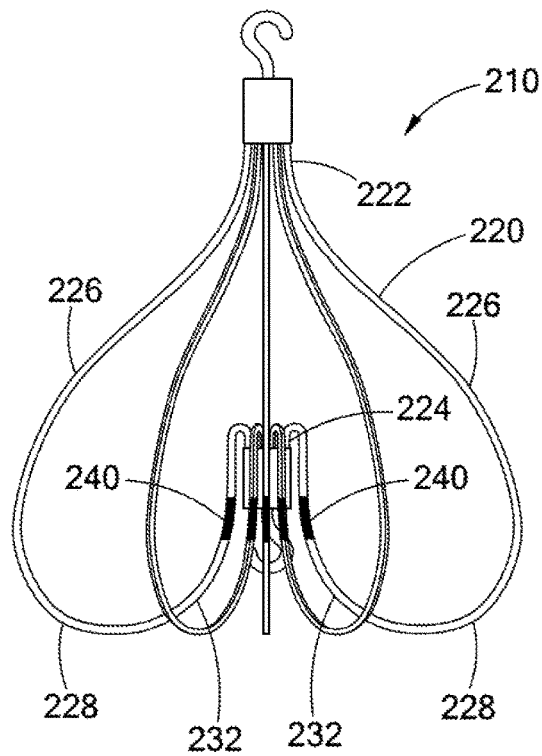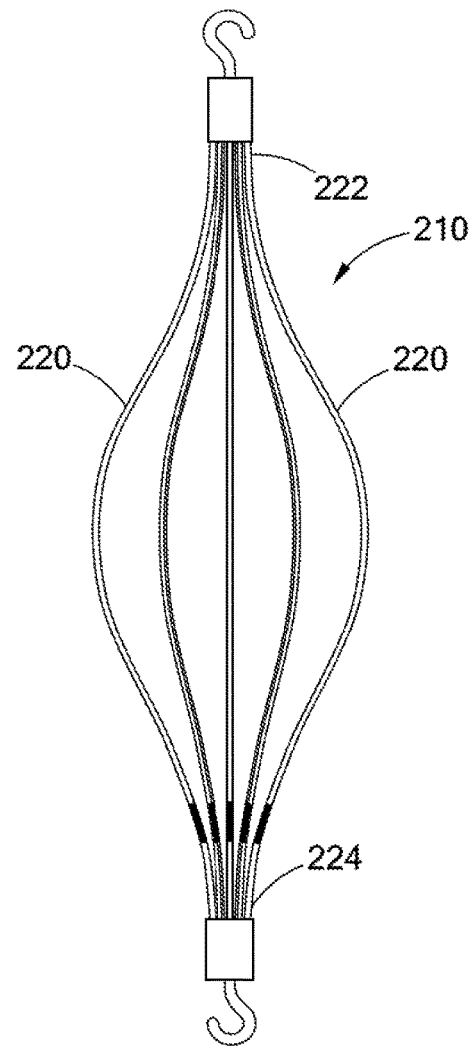
Fig. 10a
Fig. 10b

CONICAL VENA CAVA FILTER WITH JUGULAR OR FEMORAL RETRIEVAL

CROSS-REFERENCE TO RELATED APPLICATIONS

This application is a Divisional of U.S. patent application Ser. No. 13/542,902, filed Jul. 6, 2012, which is incorporated by reference herein its entirety.

BACKGROUND

The present invention relates to medical devices. More particularly, the invention relates to a removable intravascular filter that can be removed from the vena cava of a patient through the patient's jugular or femoral vein.

Filtering devices that are percutaneously placed in the vena cava have been available for a number of years. A need for such filtering devices arises in trauma patients, orthopedic surgery patients, neurosurgery patients, or in patients having medical conditions requiring bed rest or non-movement. Patients having such medical conditions face an increased risk of thrombosis in the peripheral vasculature, wherein thrombi break away from the vessel wall, risking downstream embolism or embolization. For example, depending on the size, such thrombi pose a serious risk of pulmonary embolism wherein blood clots migrate from the peripheral vasculature through the heart and into the lungs.

Historically, vena cava filters were considered to be permanent implants and remained implanted in the patient for life. More recently, removable vena cava filters have been developed. These filters may be removed from the patient's vena cava after the condition or medical problem that required the device has passed.

The benefits of vena cava filters, and particularly removable vena cava filters, have been well established, but improvements may be made. For example, the vast majority of the removable vena cava filters currently on the market must be removed through the patient's jugular vein. In some instances, however, removal through the patient's femoral vein is preferable to removal through the jugular vein. For example, filters sometimes shift or become stuck in a patient's vena cava. The ability to retrieve such troublesome filters from a different access point can increase the likelihood that they will be removed successfully. In addition, jugular retrieval requires that a retrieval sheath be advanced through the patient's heart, which is contraindicated in some cases. Finally, scarring at the access point is less noticeable when retrieval is initiated through the femoral vein.

It has been a challenge to design a vena cava filter suitable for removal through a patient's femoral vein.

SUMMARY OF INVENTION

A removable intravascular filter is provided. The filter has a filtering configuration for capturing thrombi in a blood vessel and a retrieval configuration for removal from the blood vessel. The filter may be implanted in a patient's vena cava and may be removed from the vena cava through the patient's jugular or femoral vein.

The filter has a plurality of struts having first and second ends. The first ends of the struts are attached together along a longitudinal axis. Likewise, the second ends of the struts are attached together along the longitudinal axis. Each strut has a first portion, a second portion, and a third portion. The third portion of each strut has a bending region. When the filter is in the filtering configuration, the first portion extends laterally away from the longitudinal axis and generally upstream from the first end, the second portion extends generally upstream from the first portion, and the third portion extends inwardly toward the longitudinal axis and generally downstream from the second portion to the second end. When the filter is in the retrieval configuration, each strut extends generally upstream from the first end to the second end. The filter also includes a first coupling element disposed with the first ends of the struts for jugular vein retrieval and a second coupling element disposed with the second ends of the struts for femoral vein retrieval.

A method of removing an intravascular filter from a patient's vena cava through the patient's femoral vein is also provided. The method is preferably employed with the filter described above. In practicing the method, a retrieval assembly including a retrieval sheath and a control member is percutaneously inserted into the patient's vasculature through the patient's femoral vein. The retrieval assembly is advanced through the patient's vasculature to a retrieval position proximal to the intravascular filter in the patient's vena cava. The control member of the retrieval assembly is attached to the second coupling element of the intravascular filter. Retraction of the control member proximally through the retrieval sheath applies tension to the second coupling element, moving the intravascular filter from the filtering configuration to a retrieval configuration. A retrieval sheath is then advanced distally over the intravascular filter, and both the retrieval assembly and intravascular filter are removed from the patient's vasculature.

Further objects, features, and advantages of the present invention will become apparent from consideration of the following description and the appended claims when taken in connection with the accompanying drawings.

BRIEF DESCRIPTION OF THE DRAWINGS

FIGS. 2a and 2b are partial side views of the filter shown in FIGS. 1a and 1b, illustrating a bending region of a filter strut configured as a narrowed portion of the strut;

FIGS. 3a-3c are partial side views of the filter shown in FIGS. 1a and 1b, illustrating a bending region of a filter strut configured as a mechanical hinge;

FIGS. 4a and 4b are partial side views of the filter shown in FIGS. 1a and 1b, illustrating angular joints configured as mechanical hinges;

FIGS. 5a and 5b are partial side views of two embodiments of the filter shown in FIGS. 1a and 1b, showing two different coupling element configurations;

FIGS. 10a and 10b are side views of another embodiment of an intravascular filter in the filtering and retrieval configurations, respectively.

DETAILED DESCRIPTION

A removable intravascular filter is provided. The filter has a filtering configuration for capturing thrombi in a blood vessel and a retrieval configuration for removal from the blood vessel. The filter may be implanted in a patient's vena cava and may be removed from the vena cava through the patient's jugular or femoral vein. A method of removing an intravascular filter from a patient's vena cava through the patient's femoral vein is also provided.

As used herein, the terms "upstream" and "downstream" refer to the direction of blood flow in a patient's vasculature. When these terms are used to describe the elements of an intravascular filter, they suggest a preferred orientation of the filter in the patient's vasculature. However, these terms are not intended to be limiting in this regard. In other words, a filter otherwise including the structural elements recited herein will not be deemed to fall outside the scope of the present invention merely because it is implanted in a different orientation.

Figure 1A:
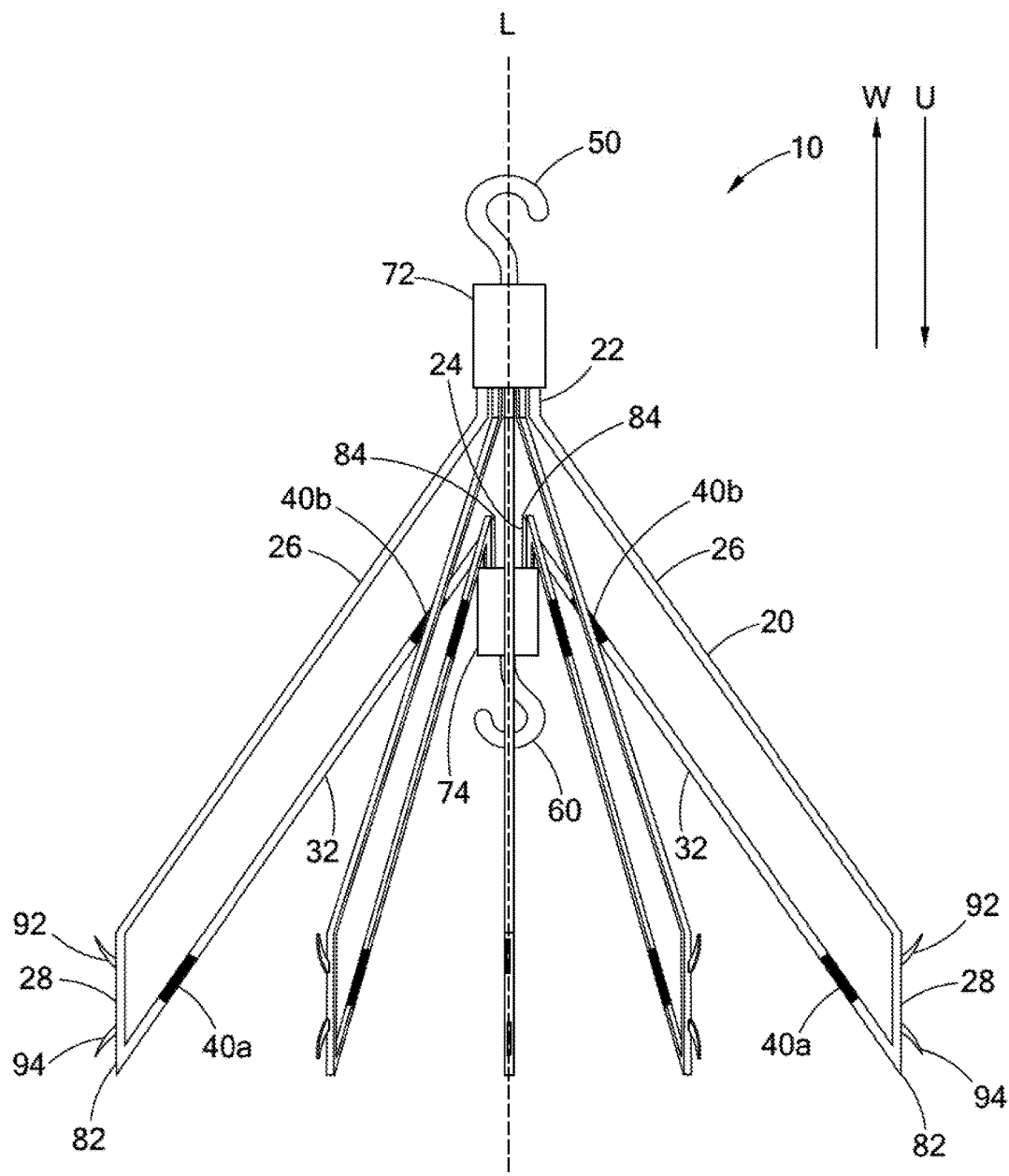
FIGS. 1a and 1b are side views of an intravascular filter in the filtering and retrieval configurations, respectively.
Figure 1B:
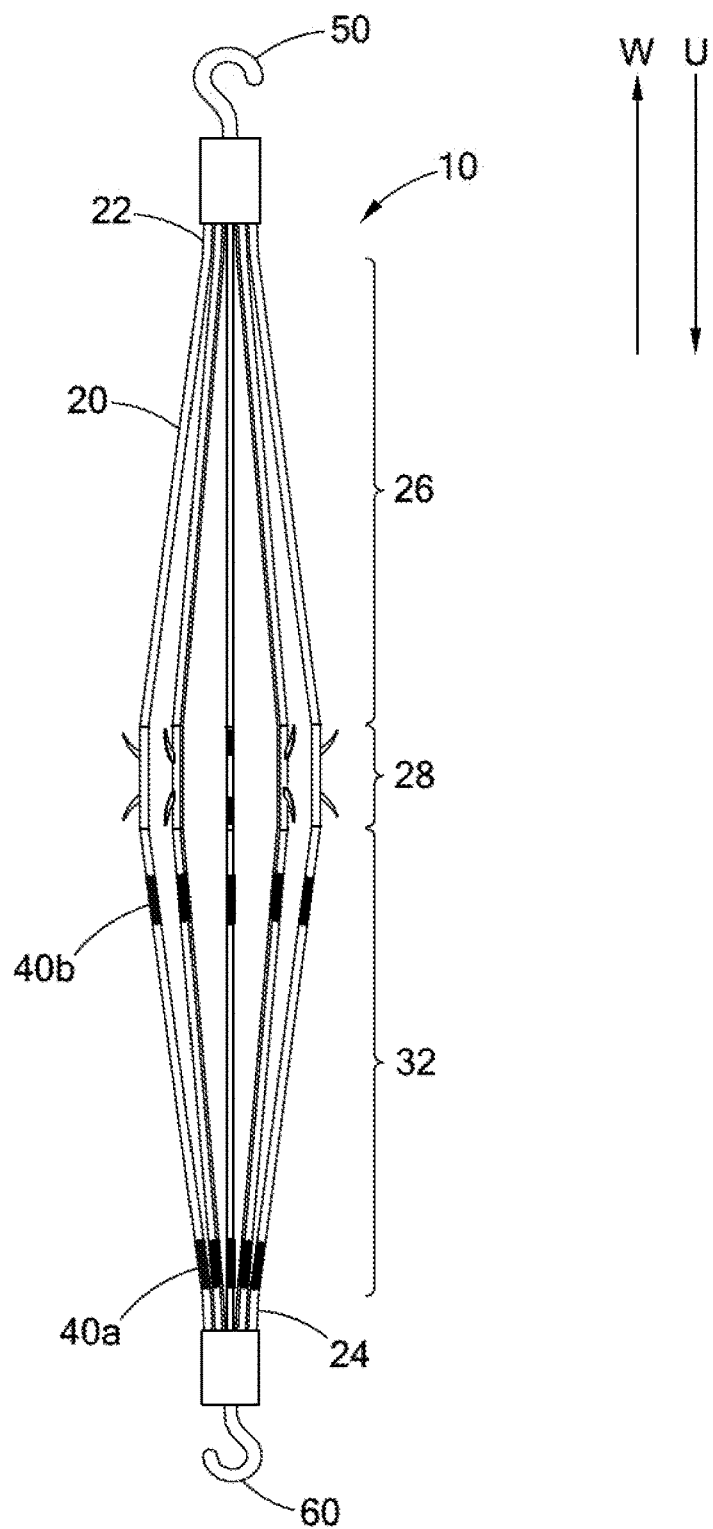
Figure 6:
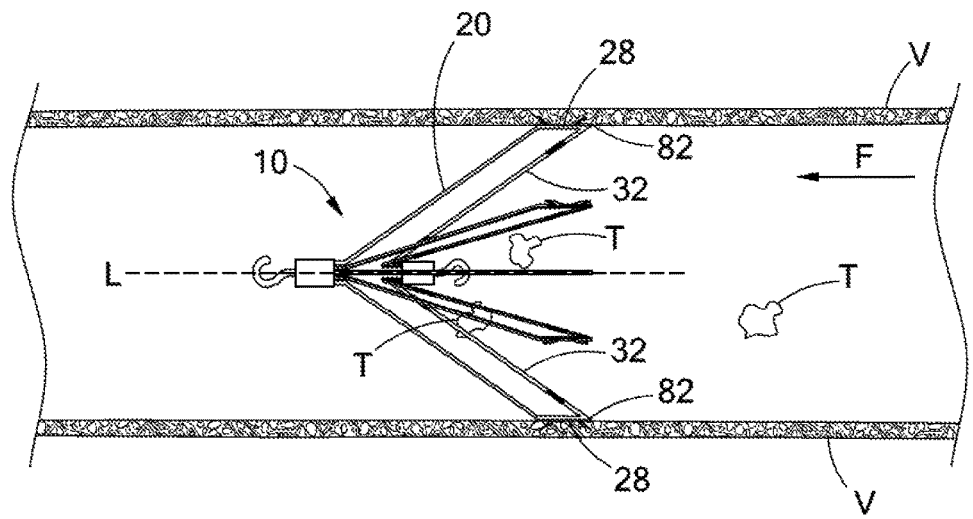
FIG. 6 is an environmental view of the filter shown in FIGS. 1a and 1b, illustrating the filter capturing thrombi in a patient's blood vessel.

FIGS. 1a and 1b illustrate side views of an intravascular filter 10. FIG. 1a illustrates the filter 10 in a filtering configuration suitable for capturing thrombi in a patient's blood vessel. FIG. 1b illustrates the filter 10 in a retrieval configuration suitable for delivery to or retrieval from the patient's blood vessel. In FIGS. 1a and 1b, the upstream direction is indicated by the arrow U, and the downstream direction is indicated by the arrow W.

The filter 10 comprises a plurality of struts 20. Each strut 20 has a first end 22 and a second end 24. The first ends 22 of the struts 20 are attached together along the longitudinal axis L of the filter 10. Progressing from the first end 22 toward the second end 24, each strut 20 has a first portion 26, a second portion 28, and a third portion 32. The second ends 22 of the struts 20 are attached together along the longitudinal axis L of the filter 10. A first coupling element 50 is disposed with the first ends 22 of the struts 20 for jugular vein retrieval of the filter 10. Correspondingly, a second coupling element 60 is disposed with the second ends 24 of the struts 20 for femoral vein retrieval of the filter 10.

The filter 10 may have any suitable number of struts 20 without falling beyond the scope of the present invention. For example, the filter 10 may have between 4 and 16 struts. Preferably, the filter 10 has between 6 and 8 struts. The struts 20 may be evenly spaced around the longitudinal axis L of the filter 10, but the struts 20 may also be unevenly spaced without falling beyond the scope of the present invention.

When the filter 10 is in the filtering configuration, as shown in FIG. 1a, the first portion 26 of each strut 20 extends laterally away from the longitudinal axis L and upstream from the first end 22 of the strut 20. The first portion 26 of each strut 20 extends substantially linearly away from the first end 22, and at a diagonal to the longitudinal axis L. However, it will be understood that the first portions 26 of the struts 20 may also extend arcuately from the first ends 22 to the second portions 28 without falling beyond the scope of the present invention. For example, the first portion 26 may define an outwardly-curving arc such that the slope of the strut 20 relative to the longitudinal axis L increases along the first portion 26 of the strut 20 when progressing away from the first end 22. Alternatively, the first portion 26 may define an inwardly-curving arc such that the slope of the strut 20 relative to the longitudinal axis L decreases along the first portion 26 of the strut 20 when progressing away from the first end 22.

It will also be understood that some regions of the first portion 26 may actually extend downstream without falling beyond the scope of the present invention, so long as the first portion 26 extends generally upstream from the first end 22 of the strut 20. A portion of a strut 20 will be understood to extend "generally upstream" or "generally downstream" if the portion primarily extends upstream or downstream, respectively, even if the portion does not extend upstream or downstream, respectively, in a particular region along its length.

Referring again to FIG. 1a, the second portion 28 of each strut 20 extends upstream from the first portion 26 of the strut 20. In the embodiment shown in FIG. 1a, the first and second portions 26 and 28 of the struts 20 define an angular joint. However, it will be understood that the first and second portions 26 and 28 may also be smoothly joined without falling beyond the scope of the present invention.

The second portions 28 of the struts 20 preferably extend substantially in parallel to the longitudinal axis L of the filter 10. The second portion 28 of a strut 20 shall be deemed to extend "substantially in parallel" to the longitudinal axis L of the filter 10 if the angle between the longitudinal axis L and a line coinciding with the second portion 28 of the strut 20 does not exceed 10°. The substantially parallel relationship between the second portions 28 of the struts 20 and the longitudinal axis L allows the second portions 28 of the struts 20 to more-firmly engage the blood vessel walls when the filter 10 is implanted in a patient's blood vessel. However, it will be understood that the second portions 28 of the struts 20 may also have a non-parallel relationship with the longitudinal axis L and/or may have an arcuate shape without falling beyond the scope of the present invention. It will also be understood that some regions of the second portion 28 may actually extend downstream without falling beyond the scope of the present invention, so long as the second portion 28 extends generally upstream from the first portion 26 of the strut 20.

The second portions 28 of the struts 20 include first and second anchoring hooks 92 and 94 to engage the blood vessel wall when the filter 10 is deployed in the filtering configuration in a patient's blood vessel. The first anchoring hooks 92 extend away from the longitudinal axis L of the filter 10 and downstream in order to prevent downstream migration of the filter 10. The second anchoring hooks 94 extend away from the longitudinal axis L of the filter 10 and upstream in order to prevent upstream migration of the filter 10 when tension is applied to the second coupling element 60 during retrieval of the filter 10 through the patient's femoral vein. The anchoring hooks 92 and 94 may be unitarily formed with the struts 20 or may be fixedly attached to the struts 20 by any means known to those having ordinary skill in the relevant art. In some embodiments, the anchoring hooks 92 and 94 may be designed to be collapsible to facilitate retrieval of the filter 10 from the patient's vasculature.

Referring again to FIG. 1a, the third portion 32 of each strut 20 extends inwardly toward the longitudinal axis L and downstream from the second portion 28 of the strut 20 to the second end 24 of the strut 20. Preferably, the third portion 32 of each strut 20 extends substantially linearly from the second portion 28 toward the second end 24, and at an angle relative to the longitudinal axis L. However, it will be understood that the third portion 26 may also extend arcuately from the second portion 28 to the second end 24. For example, the third portion 32 may define an outwardly-curving arc such that the slope of the strut 20 relative to the longitudinal axis L decreases along the third portion 32 of the strut 20 when progressing from the second portion 28 to the second end 24. Alternatively, the third portion 32 may define an inwardly-curving arc such that the slope of the strut 20 relative to the longitudinal axis L increases along the third portion 32 of the strut 20 when progressing from the second portion 28 to the second end 24. It will also be understood that some regions of the third portion 32 may actually extend upstream without falling beyond the scope of the present invention, so long as the third portion 32 extends generally downstream from the second portion 28 to the second end 24 of the strut 20.

Referring now to FIG. 1b, when the filter 10 is in the retrieval configuration, each strut 20 extends generally upstream from the first end 22 to the second end 24. Preferably, as shown in FIG. 1b, each strut 20 extends monotonically upstream from the first end 22 to the second end 24. As used herein, a strut 20 shall be understood to extend "monotonically upstream" from its first end 22 to its second end 24 where, progressing from the first end 22 to the second end 24, the strut 20 is extending upstream at all points along the strut 20. In other words, progressing from the first end 22 to the second end 24, each point along the strut 20 is further upstream than the last.

The third portion 32 of each strut 20 also includes one or more bending regions 40. As discussed below, the bending regions 40 are configured to bend when tension is applied to the second coupling element 60 so that the filter 10 can move more easily from the filtering configuration to the retrieval configuration. In some embodiments, the third portion 32 includes a plurality of bending regions 40. For example, in the filter 10 shown in FIGS. 1a and 1b, the third portion 32 has a first bending region 40a and a second bending region 40b. The first bending region 40a is disposed adjacent to the second portion 28 of the strut 20. The second bending region 40b is disposed adjacent to the second end 24 of the strut 20.

The bending region 40 may have any structure suitable to impart enhanced flexibility to the strut 20. Thus, the bending region 40 may be a narrowed portion of the strut 20, a mechanical hinge, or any other structure known in the art to impart enhanced flexibility to an elongate member.

As shown in FIGS. 2a-2b, the bending region 40 may comprise a narrowed portion 41 of the strut 20. The narrowed portion 41 of the strut 20 is a region of the strut 20 having a reduced cross-sectional dimension. Thus, where the strut 20 generally has a cross-sectional dimension $D_1$, the bending region has a reduced cross-sectional dimension $D_2$. As shown in FIG. 2a, the narrowed portion 41 may be centered relative to the strut 20. Alternatively, as shown in FIG. 2b, the narrowed portion 41 may be off-center relative to the strut 20.

As a person having ordinary skill in the art will understand, the bending region 40 may comprise a narrowed portion regardless of the cross-sectional shape of the strut 20. For example, where the strut 20 has a round cross-section, the cross-sectional dimension may be defined as the cross-sectional diameter of the strut 20. Similarly, where the strut 20 has a square or rectangular cross-section, the cross-sectional dimension may be defined as the length of one or both legs of the square or rectangle. In any case, the reduced cross sectional dimension $D_2$ in the bending region 40 defines the narrowed portion 41 of the strut 20.

Referring now to FIGS. 3a-3c, the bending region 40 may comprise a mechanical hinge 42. Where the bending region 40 is a mechanical hinge 42, the strut comprises a first member 44 and a second member 46 connected at the mechanical hinge 42. As most clearly shown in FIG. 3b, the first member 44 includes a tongue 45. The second member 46 includes a groove 47 defined by two shoulders 49. The groove 47 is sized to receive the tongue 45 between the two shoulders 49. A pin 48 passes through the shoulders 49 and the tongue 45 to hold the tongue 45 in the groove 47, securing the first member 44 to the second member 46. The tongue 45 and shoulders 49 are preferably both free to rotate on the pin 48, such that the hinge 42 allows the strut to bend at the bending region 40 by rotational movement of the first member 44 relative to the second member 46.

As a person having ordinary skill in the art will understand, the hinge 42 generally restricts the relative rotational motion of the first and second members 44 and 46 to a single plane. Depending on the design of the hinge 42, such motion may be further restricted. As shown in FIG. 3a, the shoulder 49 of the second member 46 may be rounded on both sides, such that the hinge 42 is free to bend in both directions within the plane. Alternatively, as shown in FIG. 3c, the shoulder 49 of the second member 46 may be squared off on one side, such that the hinge 42 is only permitted to bend in the direction indicated by the arrow A.

By employing the hinge 42 described above with reference to FIG. 3c, or any other suitable means known to those having ordinary skill in the relevant art, a given bending region 40 of the filter 10 may be configured to bend in a preselected direction relative to the longitudinal axis of the filter 10. For example, referring again to FIG. 1a, the first bending region 40a may be configured to bend toward the longitudinal axis L when the filter 10 is in the filtering configuration, and tension is applied to the second coupling element 60. Similarly, the second bending region 40b may be configured to bend away from the longitudinal axis L when the filter 10 is in the filtering configuration, and tension is applied to the second coupling element 60. It will be understood, however, that the first and second bending regions 40a and 40b may be configured to bend in any other combination of directions without falling beyond the scope of the present invention. As used herein, a bending region 40 will be understood to bend in a particular direction (e.g., toward the longitudinal axis) when the bending of the bending region 40 causes the bending region 40 itself to move in that particular direction.

Referring again to FIG. 1a, the second and third portions 28 and 32 of each primary strut 20 preferably define a first angular joint 82 when the filter 10 is in the filtering configuration. The first angular joint 82 preferably defines an acute angle between the second and third portions 28 and 32. The first angular joint 82 may simply comprise an angular bend in the strut 20 between the second and third portions 28 and 32. Alternatively, as shown in FIG. 4a, the first angular joint 82 may be a mechanical hinge situated between the second and third portions 28 and 32 of the strut 20. The mechanical hinge making up the first angular joint may be constructed as in the same manner as the hinge 42 described above with reference to FIGS. 3a-3c.

In some embodiments, as shown in FIG. 1a, the third portion 32 includes a second angular joint 84 directly adjacent to the second end 24 of the strut 20. Like the second angular joint 82, the third angular joint 84 may be a simple angular bend or a mechanical hinge, as shown in FIG. 4b. Where the third portion 32 includes a second angular joint 84, the third portion 32 of the strut may extend upstream between the second angular joint 84 and the second end 24, as shown in FIG. 1a. However, even where this is the case, the third portion 32 will still be understood to extend inwardly toward the longitudinal axis L and generally downstream from the second portion 28 to the second end 24.

The filter 10 may be constructed from any suitable material and by any means known to those having ordinary skill in the relevant art without falling beyond the scope of the present invention. Preferably, the filter 10 is constructed from a superelastic material, a nickel-titanium alloy (e.g., NITINOL), stainless steel, cobalt-chromium-nickel-molybdenum-iron alloy, cobalt-chrome alloy, or nickel-chromium alloy.

In some embodiments, the filter 10, including the struts 20 and the first and second coupling elements 50 and 60 are constructed from a laser cut cannula, e.g., a nickel-titanium alloy cannula. The cannula from which the filter 10 is cut may have any suitable diameter. The cannula preferably has a diameter between about 1.5 mm and about 2.5 mm, and more preferably has a diameter between about 1.7 mm and about 2.0 mm. In these embodiments, the filter 10 may, but need not, further comprise hubs housing the ends of the cannula.

In other embodiments, the struts 20 of the filter 10 are constructed from stainless steel, nickel-titanium alloy, or nickel-chromium (e.g., INCONEL) wire. In these embodiments, the filter 10 preferably further comprises a first hub housing the first ends 22 of the struts 20, and a second hub 74 housing the second ends 24 of the struts 20.

Referring now to FIGS. 5a and 5b, the first and second coupling elements 50 and 60 are described in greater detail. As shown in FIG. 5a, where the filter 10 is constructed from a laser cut cannula, the coupling elements 50 and 60 may comprise diagonal notches 52 and 62, respectively, in the walls of the cannula. Alternatively, as shown in FIG. 5b, where the struts 20 are constructed from a wire material, and the ends of the struts are housed in the hubs 72 and 74, the coupling elements 50 and 60 may comprise a jugular retrieval hook 54 extending downstream from the first hub 72 and a femoral retrieval hook 64 extending upstream from the second hub 74, respectively.

The filter 10 may be delivered to a patient's blood vessel, such as the patient's vena cava, using standard techniques familiar to those having ordinary skill in the relevant art. For example, a delivery sheath may be percutaneously inserted into the patient's vasculature via any suitable access site, such as the jugular vein, femoral vein, or any other suitable access site. Preferably, the diameter of the delivery sheath is no greater than 7 French.

The delivery sheath may be advanced through the patient's vasculature until the distal end of the delivery sheath is disposed in the patient's blood vessel at the desired site of deployment. The intravascular filter then may be disposed within the lumen of the delivery sheath in the filtering configuration with the struts collapsed along the longitudinal axis. The filter is expelled from the distal end of the delivery sheath by use of a push wire or other suitable device. Upon deployment from the distal end of the delivery sheath, the struts of the filter preferably self-expand away from the longitudinal axis until the second portions of the struts engage the blood vessel walls. While the foregoing method is provided by way of example, a person having ordinary skill in the relevant art will understand that a filter constructed in accordance with the principles of the present invention may be deployed using any other suitable technique without falling outside the scope of the present invention.

The operation and retrieval of the filter 10 will now be described with reference to FIGS. 6-9. When the filter 10 is deployed in a patient's blood vessel V in the filtering configuration, the second portions 28 of the struts 20 engage the walls of the blood vessel V, anchoring and centering the filter 10 in the blood vessel V. In this regard, the substantially parallel relationship between the second portions 28 and the longitudinal axis L of the filter 10, described above, is advantageous because it maximizes the area of contact between the struts 20 and the walls of the vessel V.

Thrombi T carried by the blood stream F are captured in the filter 10. More specifically, the thrombi T are captured along the longitudinal axis L of the filter 10. As the thrombi T enter the filter 10, the thrombi T are funneled toward the longitudinal axis L of the filter 10 by the third portions 32 of the struts 20. Several structural features of the filter 10 facilitate this funneling action. First, the first angular joints 82 create a very low profile at the upstream end of the filter 10, such that the thrombi T are unlikely to be trapped or hung up along the walls of the vessel V. Second, the angle of the third portions 32 relative to the longitudinal axis L causes the thrombi T to slide toward the longitudinal axis L as the flow of blood pushes the thrombi T downstream.

The capture of thrombi T along the longitudinal axis L of the filter 10 is advantageous for several reasons. First, because blood flow is greatest near the center of the blood vessel V, thrombi T captured near the center of the vessel are more likely to dissolve after capture. Second, thrombi T captured along the wall of the blood vessel V tend to grow by accumulating additional clot material, and can eventually occlude the vessel.

After the risk of embolism has subsided, the filter 10 may be removed from the blood vessel V through either the patient's jugular vein or femoral vein. The filter 10 may be removed through the patient's jugular vein using procedures that are well known to those having ordinary skill in the relevant art. For example, the filter 10 may be removed through the patient's jugular vein using the method described in U.S. Pat. No. 7,625,390, the entire contents of which are incorporated herein by reference.

Alternatively, the filter 10 may be removed through the patient's femoral vein. Advantageously, all thrombi T are removed from the filter 10 before removal of the filter 10 through the patient's femoral vein. In some cases, the flow of blood F through the filter dissolves the thrombi T captured in the filter 10. In other cases, it may be necessary to remove the thrombi by aspiration through a catheter.

Figure 7:
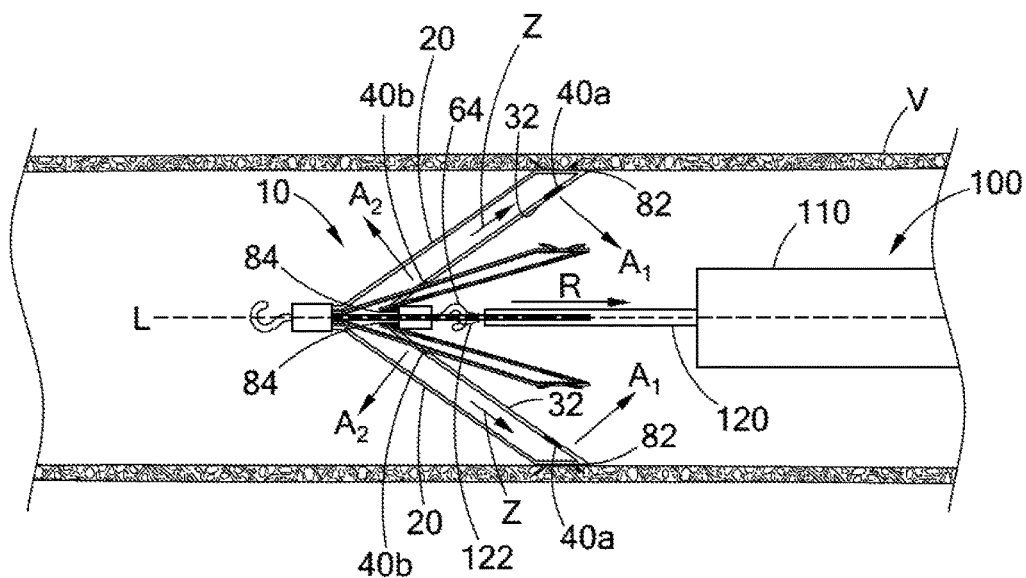
FIGS. 7-9 are environmental views of the filter shown in FIGS. 1a and 1b, illustrating the movement of the filter from the filtering configuration to the retrieval configuration.

After all remaining thrombi T have been removed from the filter 10, the removal of the filter 10 is initiated by inserting a retrieval assembly 100 into the patient's vasculature through the patient's femoral vein. Referring now to FIG. 7, the retrieval assembly 100 includes a retrieval sheath 110. The retrieval sheath 110 preferably has a diameter of 8-9 French, but other sizes of retrieval sheath may be used. The retrieval assembly 100 further comprises a control member 120 disposed in the lumen of the retrieval sheath 110. The control member 120 has a snare 122 disposed at its distal end.

Referring again to FIG. 7, the retrieval assembly 100 is advanced through the patient's vasculature to a position immediately upstream of the filter 10 in the patient's blood vessel V. The control member 120 is advanced from the lumen of the retrieval sheath 110, and the snare 122 is attached to the second coupling element, in this case the femoral retrieval hook 64. The control member 120 is then retracted in the direction of the arrow R, applying tension to the retrieval hook 64.

As described above, the first and second bending regions 40a and 40b of the third portion 32 of the strut 20 are preferably configured to bend in a first direction $A_1$ toward the longitudinal axis L of the filter 10 and in a second direction $A_2$ away from the longitudinal axis L of the filter 10, respectively. This bending action allows the struts 20 to move from the filtering configuration to the retrieval configuration without applying excessive force to the walls of the blood vessel.

More specifically, as tension is applied to the femoral retrieval hook 64 by the retraction of the control member 120, the first bending regions 40a bend in the first direction $A_1$ toward the longitudinal axis L. This bending causes the third portions 32 of the struts 20 to rotate counter-clockwise relative to the first angular joints 82. Similarly, the second bending regions 40b bend in the second direction $A_2$ away from the longitudinal axis L, causing the third portions 32 of the struts 20 to rotate counter-clockwise relative to the second angular joints 84.

Figure 8:
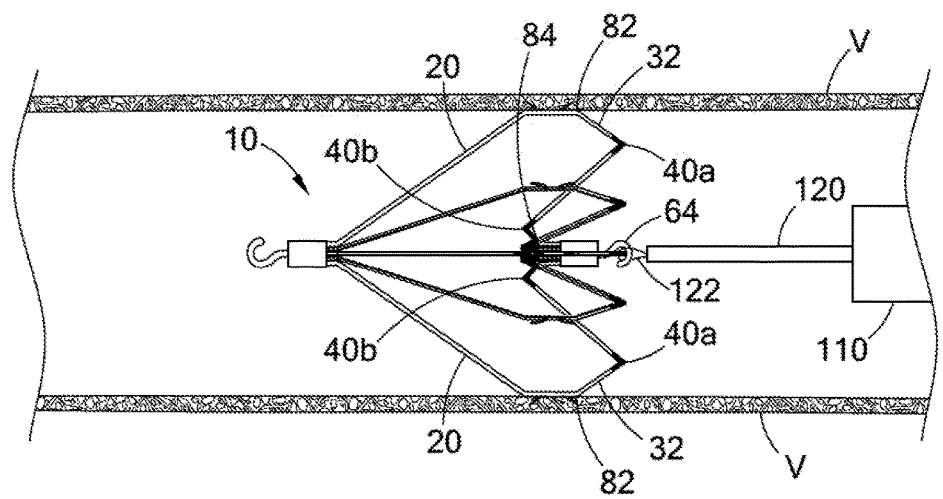
Figure 9:
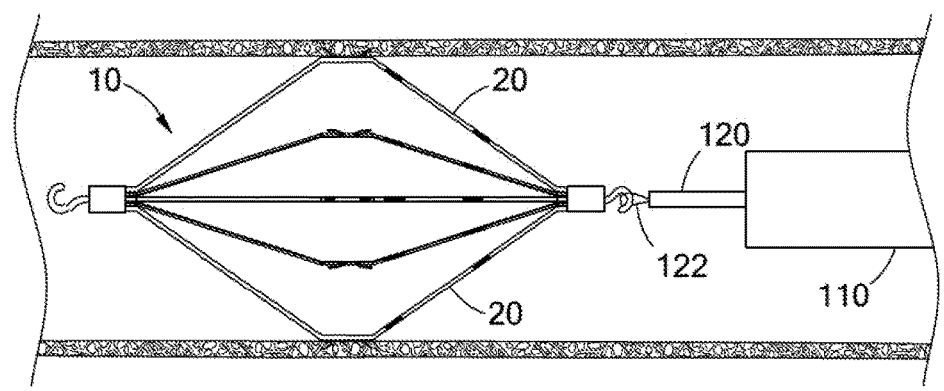

As the third portions 32 of the struts 20 rotate counter-clockwise relative to the first and second angular joints 82 and 84, the filter 10 begins to move from the filtering configuration to the retrieval configuration as shown in FIG. 8. As the retraction of the control member 120 continues, the tension applied to the femoral retrieval hook ultimately causes the bending regions 40a and 40b to straighten until the filter 10 reaches the retrieval configuration, as shown in FIG. 9.

As will be apparent from the foregoing discussion, the bending regions 40 of the struts 20 are important to the operation of the filter 10 when the filter 10 includes first angular joints 82. Absent the bending regions 40, an operator would have difficulty moving the filter 10 from the filtering configuration to the retrieval configuration without exerting excessive force on the walls of the patient's blood vessel. The tension applied to the second coupling element, e.g., to the hook 64, is transmitted to the third portions 32 of the struts 20 along the force vector Z. Absent the bending regions 40, the force Z would be transmitted into the walls of the blood vessel V. With the bending regions 40, the force Z causes the third portions 32 of the struts 20 to bend so that the filter 10 may move to the retrieval configuration.

Once the filter 10 is in the retrieval configuration, the retrieval sheath 110 is advanced over the filter 10. The filter 10 is held in place by the control member 120 and the snare 122. The retrieval sheath 110 is advanced over the struts 20. As the retrieval sheath 110 contacts the struts 20, the filter 10 collapses and is received into the lumen of the retrieval sheath 110. Once the filter 10 is stowed in the lumen of the retrieval sheath 110, the retrieval assembly 100 and the filter 10 may be removed from the patient's vasculature.

FIGS. 10a and 10b illustrate side views of an intravascular filter 210. Unless otherwise specified, the structural features and operation of the filter 210 are the same as those of the filter 10, as described above. The filter 210 comprises a plurality of struts 220. Each strut has a first end 222 and a second end 224. Progressing from the first end 222 to the second end 224, each strut has a first curved portion 226, a second curved portion 228, and a third curved portion 232. As shown in FIG. 10a, each strut 220 extends arcuately from the first end 222 to the second end 224 when the filter 210 is in the filtering configuration. As shown in FIG. 10b, the struts 220 extend generally upstream from the first ends 222 to the second ends 224 when the filter 210 is in the retrieval configuration.

Referring again to FIG. 10a, the filtering configuration of the filter 210 is described. The first curved portion 226 extends laterally away from the longitudinal axis of the filter 210 and upstream from the first end 222 and curves back toward the longitudinal axis. The second curved portion 228 extends inwardly toward the longitudinal axis and upstream from the first curved portion 226 and curves back downstream. The third curved portion 232 extends inwardly toward the longitudinal axis and downstream from the second curved portion 228 to the second end 224 of the strut 220. The third curved portions 232 of one or more struts 220 include bending regions 240.

Figure 11:
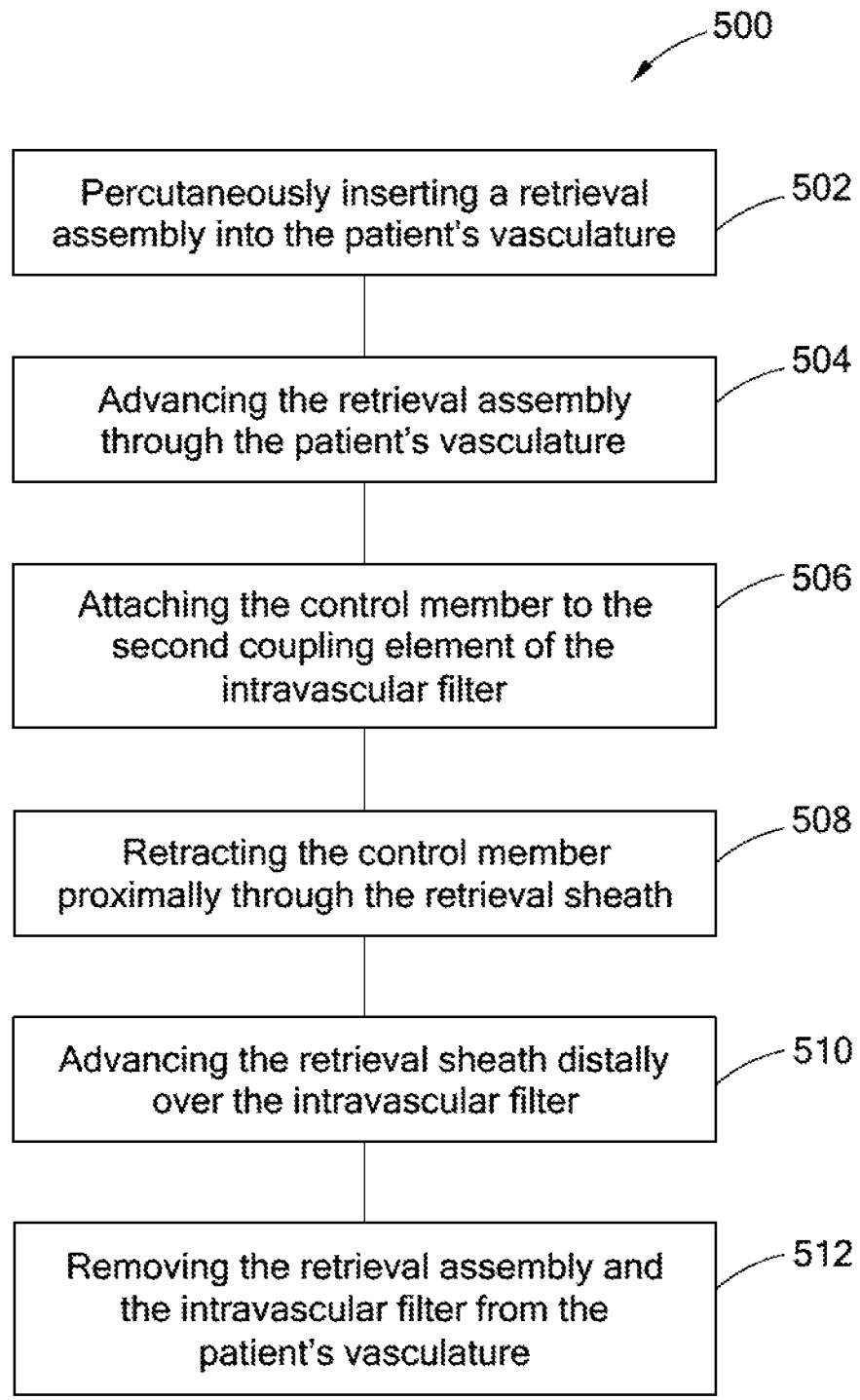
FIG. 11 is a flow chart depicting a method of retrieving an intravascular filter from a patient's vena cava through the patient's femoral vein.

Referring now to FIG. 11, a method 500 for retrieving an intravascular filter, such as the filter 10, from a patient's vena cava through the patient's femoral vein is provided. As indicated in box 502, the method 500 involves percutaneously inserting a retrieval assembly, such as the retrieval assembly 100, into the patient's vasculature through the patient's femoral vein. The retrieval assembly includes a retrieval sheath and a control member.

As indicated in box 504, the method 500 further comprises advancing the retrieval assembly through the patient's vasculature to a retrieval position proximal to the intravascular filter in the patient's vena cava. The control member of the retrieval assembly is then attached to the second coupling element of the intravascular filter, as indicated in box 506. Where the control member includes a snare loop (e.g. the control member 120) and the second coupling element is a hook (e.g., the femoral retrieval hook 64), the control member may be attached to the second coupling element by placing the snare loop over the hook.

As indicated in box 508, the method 500 further comprises retracting the control member proximally through the retrieval sheath to apply tension to the second coupling element. The tension moves the intravascular filter from the filtering configuration to a retrieval configuration, in which each strut extends upstream from its first end to its second end. The tension applied to the second coupling element may cause the bending regions of the struts to bend, allowing the intravascular filter to move from the filtering configuration to the retrieval configuration without exerting excessive force on the walls of the blood vessel. The bending region may bend away from the longitudinal axis or toward the longitudinal axis.

Once the filter is in the retrieval configuration, the retrieval sheath may be advanced over the intravascular filter as indicated in box 510. With the filter stowed in the lumen of the retrieval sheath, the retrieval assembly and the intravascular filter are removed from the patient's vasculature as indicted in box 512.

While the present invention has been described in terms of certain preferred embodiments, it will be understood that the invention is not limited to the disclosed embodiments, as those having skill in the art may make various modifications without departing from the scope of the following claims.

What is claimed is:

1. A method for retrieving an intravascular filter from a patient's vena cava through the patient's femoral vein, the method comprising:

percutaneously inserting a retrieval assembly into the patient's vasculature through the patient's femoral vein, the retrieval assembly comprising a retrieval sheath and a control member;

advancing the retrieval assembly through the patient's vasculature to a retrieval position proximal to the intravascular filter in the patient's vena cava, the intravascular filter being in a filtering configuration and comprising:

a plurality of struts having first and second ends, the first ends of the struts being attached together along a longitudinal axis, the second ends of the struts being attached together along the longitudinal axis, each strut having a first portion, a second portion, and a third portion, the third portion of each strut being substantially linear and having a bending region substantially straight in the filtering configuration, the first portion extending laterally away from the longitudinal axis and generally upstream from the first end, the second portion extending generally upstream from the first portion, the third portion extending inwardly toward the longitudinal axis and generally downstream from the second portion to the second end, the first portion and the third portion being substantially parallel in the filtering configuration;

a first coupling element disposed with the first ends of the struts for jugular vein retrieval; and a second coupling element disposed with the second ends of the struts for femoral vein retrieval;

attaching the control member to the second coupling element of the intravascular filter;

retracting the control member proximally through the retrieval sheath to apply tension to the second coupling element, the tension moving the intravascular filter from the filtering configuration to a retrieval configuration, each strut extending generally upstream from the first end to the second end when the filter is in the retrieval configuration;

advancing the retrieval sheath distally over the intravascular filter; and removing the retrieval assembly and the intravascular filter from the patient's vasculature.

2. The method of claim 1, wherein said moving the intravascular filter from the filtering configuration to the retrieval configuration comprises bending the bending region of each strut.

3. The method of claim 2, wherein said bending the bending region comprises bending the bending region away from the longitudinal axis.

4. The method of claim 2, wherein said bending the bending region comprises bending the bending region toward the longitudinal axis.

5. The method of claim 1, wherein the second portion is shorter than each of the first portion and the third portion.

* * * * *

UNITED STATES PATENT AND TRADEMARK OFFICE
CERTIFICATE OF CORRECTION

PATENT NO.       : 10,456,234 B2
APPLICATION NO.  : 15/479374
DATED            : October 29, 2019
INVENTOR(S)      : Jason C. Urbanski et al.

Page 1 of 1

It is certified that error appears in the above-identified patent and that said Letters Patent is hereby corrected as shown below:

On the Title Page

Item (73) Assignee: "Cook Medical Technolgies, Inc." should be --Cook Medical Technologies LLC--.

Signed and Sealed this
Fourteenth Day of July, 2020

Andrei Iancu
*Director of the United States Patent and Trademark Office*